US00PP32256P3

(12) United States Plant Patent
Rattanasophon

(10) Patent No.: US PP32,256 P3
(45) Date of Patent: Sep. 29, 2020

(54) ***CURCUMA* PLANT NAMED 'CPH CORAL'**

(50) Latin Name: ***Curcuma* hybrid**
Varietal Denomination: CPH Coral

(71) Applicant: Chiangmai Plants and Herbs Co., Ltd., Chiangmai (TH)

(72) Inventor: Sasirin Rattanasophon, Chiangmai (TH)

(73) Assignee: Chiangmai Plants and Herbs Co., Ltd., Chiangmai (TH)

( * ) Notice: Subject to any disclaimer, the term of this patent is extended or adjusted under 35 U.S.C. 154(b) by 0 days.

(21) Appl. No.: 16/501,638

(22) Filed: May 15, 2019

(65) Prior Publication Data

US 2019/0357404 P1 Nov. 21, 2019

Related U.S. Application Data

(60) Provisional application No. 62/762,738, filed on May 17, 2018.

(51) Int. Cl.
*A01H 5/02* (2018.01)
*A01H 6/00* (2018.01)

(52) U.S. Cl.
USPC ..... Plt./421
CPC ..... *A01H 6/00* (2018.05); *A01H 5/02* (2013.01)

(58) Field of Classification Search
USPC ..... Plt./263.1, 421
See application file for complete search history.

*Primary Examiner* — Susan McCormick Ewoldt
*Assistant Examiner* — Karen M Redden
(74) *Attorney, Agent, or Firm* — The Webb Law Firm

(57) ABSTRACT

A new and distinct *Curcuma* plant having large and light pink/coral colored inflorescences.

1 Drawing Sheet

Botanical classification: *Curcuma* hybrid.
Varietal denomination: 'CPH Coral'.

BACKGROUND OF THE INVENTION

The present invention comprises a new and distinct variety of *Curcuma* plant known by the varietal name 'CPH Coral' (previously referred to in U.S. Provisional Patent Application No. 62/762,738 as simply "Coral"). The new variety was discovered in 2017 in Chiangmai, Thailand as the result of a planned breeding program with the purposes of providing *Curcuma* plants with new coloration and characteristics. The new variety is the result of a cross between an unnamed and unpatented *Curcuma supraneena* variety (female parent) and an unnamed and unpatented *Curcuma aurantiaca* variety (male parent). The inflorescence of the new variety is similar in overall appearance to its female parent, but 'CPH Coral' exhibits larger inflorescences and leaves than its female parent. 'CPH Coral' exhibits similar inflorescence and leaf colors to its male parent, but differs from its male parent in having smaller inflorescences than its male parent. Tissue culture and bulb asexual reproductions of the new variety first occurred in 2017 in Chiangmai, Thailand. 'CPH Coral' has been trial and field tested and has been found to retain its distinctive characteristics and remain true to type through successive propagations. The present invention has not been evaluated under all possible environmental conditions. The phenotype may vary with variations in environment without a change in the genotype of the plant.

The inflorescence color and large size distinguish 'CPH Coral' from other *Curcuma* varieties known to the breeder. Further, when 'CPH Coral' is compared to *Curcuma* hybrid 'CPH Orange' (U.S. Plant patent application Ser. No. 16/501,639), the varieties are similar in plant height. However, the varieties differ in inflorescence color ('CPH Orange' has orange colored inflorescences) and 'CPH 'Orange' exhibits a red upper surface leaf midrib that is not exhibited by 'CPH Coral'.

DESCRIPTION OF THE DRAWING

The accompanying photographic drawing taken at approximately 60 days of age illustrates the new variety, with the colors being as nearly true as is possible with color illustrations of this type.

DESCRIPTION OF THE PLANT

The following detailed description sets forth the characteristics of the new variety at approximately 60 days of age. The data which defines these characteristics was collected under natural light in Chiangmai, Thailand. Plants of the new variety were grown in 20.3 cm pots in a plastic greenhouse in Chiangmai, Thailand and watered 1-2 times a day, if needed. Color references are primarily to The 2016 HTML Color Chart and The 2015 R.H.S. Colour Chart of The Royal Horticultural Society of London, 6$^{th}$ Edition, except where general color terms are used.

PLANT

Time to initiate roots: About 20-30 days at about 30-33° C.
Time to produce a rooted young plant: About 45 days at about 30-33° C.
Root description: Fibrous, with a pale yellow colored (FAFCF5) milk tank.
Number of rhizomes produced per plant: From 2-3.
Rhizome diameter: 2.0 cm.
Growth habit: Annual.
Plant height (soil level to top of inflorescences): 90.0 cm.

Plant diameter: 30.0 cm.
Pubescence: Lightly present on bracts.
Disease resistance/susceptibility: None observed.
Pest resistance/susceptibility: None observed.
Temperature tolerance: 20-40° C. or tropical climate conditions.
Drought tolerance: Unknown.
Seed/fruit: None observed to date.
Leaves:
*Arrangement*.—Alternate.
*Average number per plant*.—From 5-7.
*Length*.—24.0 cm.
*Width*.—14.0 cm.
*Shape of leaf* (*generally*).—Broadly elliptic.
*Shape of apex*.—Acuminate.
*Shape of base*.—Obtuse.
*Margin description*.—Entire.
*Texture*.—Upper surface: Smooth. Lower surface: Slight pubescence present.
*Aspect*.—Upright.
*Color*.—Young leaves: Upper surface: Light green (74AF1B). Lower surface: Green (689907). Mature leaves: Upper surface: Green (96B365). Lower surface: Green (96B365).
*Veins*.—Appearance: Pinnate and penninerved. Color: Upper surface: Green (688542). Lower surface: Green (6D822E).
*Leaf sheaths*.—Length: 25.0-35.0 cm. Width: 2.5 cm. Texture: Upper surface: Smooth. Lower surface: Smooth. Color: Upper surface: RHS 187D. Lower surface: RHS 187D. Venation: Pattern: Parallel. Color: RHS 135D.

INFLORESCENCE

Inflorescence arrangement: 1 inflorescence per shoot.
Inflorescence number per plant: From 2-3.
Inflorescence length: 15.0 cm.
Inflorescence diameter: 8.0 cm.
Fragrance: None.
Flower bracts:
*Total number per inflorescence*.—Approximately 25.
*Upper bracts*.—Number: Approximately 10. Length: 3.0-5.0 cm. Width: 2.5 cm. Shape: Lanceolate. Apex: Acute. Base: U-shaped. Margin: Entire. Texture: Upper surface: Smooth. Lower surface: Downy. Color: Upper surface: Pink/RHS 50C. Lower surface: Deep pink/RHS 51C.
*Lower bracts*.—Number: Approximately 15. Length: 2.0-4.0 cm. Width: 2.0 cm. Shape: Lanceolate-oblong. Apex: Acute. Base: U-shaped. Margin: Entire. Texture: Upper surface: Smooth. Lower surface: Downy. Color: Upper surface: Pink (B14B3F). Lower surface: Pink (DB7166).

Flowers:
*Number per inflorescence*.—Approximately 30.
*Continuity of flowering*.—1 month.
*Lastingness of an individual flower*.—1-2 days.
*Length*.—4.0 cm.
*Diameter*.—1.0 cm.
*Appearance*.—Orchidaceous form with a tubular base.
*Upper petals*.—Upper surface color: Yellow (FFFE57). Lower surface color: Yellow (FFFE57).
*Lower petals*.—Upper surface color: Yellow (FFFA60). Lower surface color: Yellow (FFFA60).
*Flower buds*.—Length: 4.0 cm. Diameter: 0.5 cm. Shape: Round apex, with the base connected in a cone shape. Texture: Smooth. Color: RHS 9A.
*Sepals*.—Number: 3. Calyx arrangement: In overlapping circles. Length: 1.0 cm. Width: 0.5 cm. Overall shape: Elliptic. Apex: Elliptic. Base: Connected in a cone shape. Texture: Smooth (both surfaces). Color: RHS 10D (both surfaces).
Peduncles:
*Length*.—20.0-25.0 cm.
*Diameter*.—1.0 cm.
*Texture*.—Smooth.
*Angle*.—Upright.
*Color*.—Green (827912).

REPRODUCTIVE ORGANS

Stamens:
*Number*.—1.
Filament:
*Length*.—4.0 cm.
*Diameter*.—1.0 mm.
*Color*.—White (D1D48E).
Anthers:
*Shape*.—2-lobed.
*Length*.—4.0 mm.
*Color*.—White (D1D48E).
Pollen: None observed.
Pistils:
*Number*.—1.
*Length*.—4.0 cm.
Style:
*Length*.—4.0 cm.
*Diameter*.—1.0 mm.
*Color*.—White (D1D48E).
Stigma:
*Length*.—2.0 mm.
*Diameter*.—1.0 mm.
*Color*.—White (D1D48E).

I claim:

1. A new and distinct variety of *Curcuma* plant, as is herein illustrated and described.

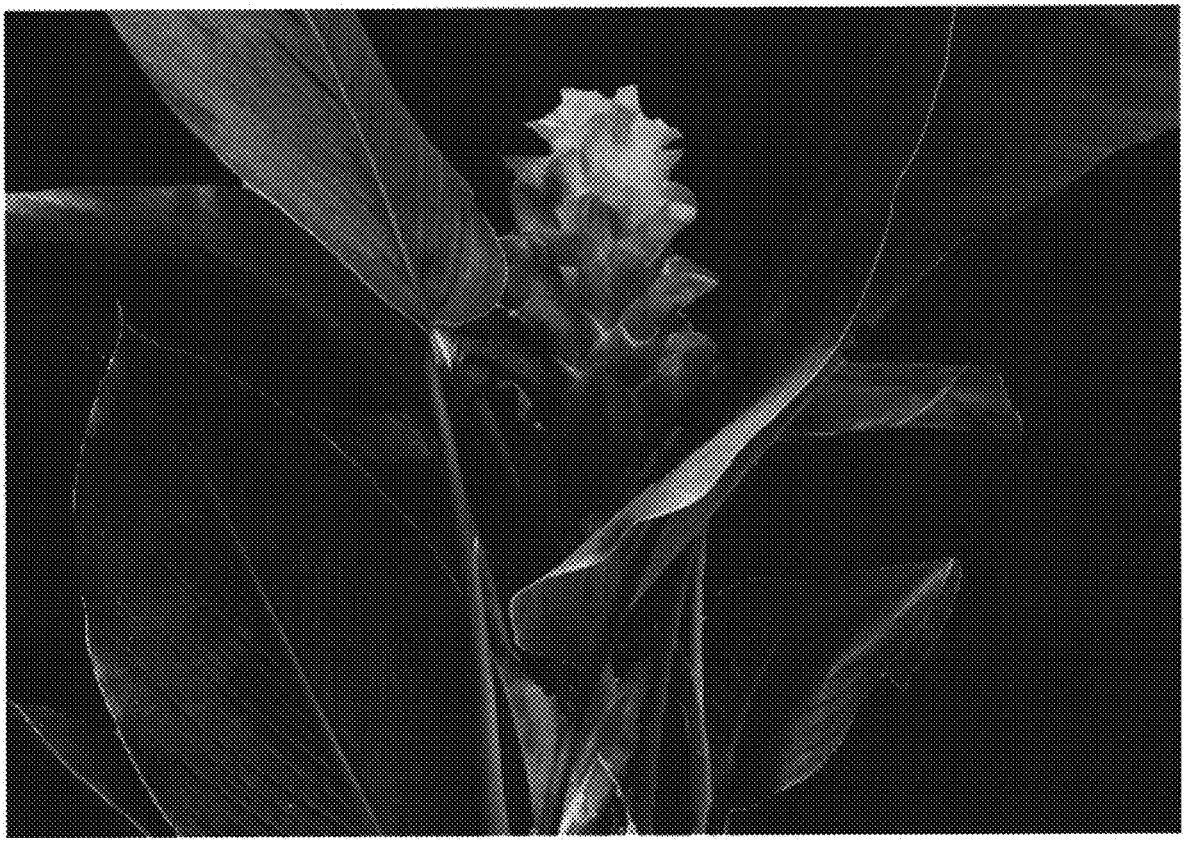

* * * * *